(12) United States Patent
Khaira

(10) Patent No.: US 8,400,295 B1
(45) Date of Patent: Mar. 19, 2013

(54) HUMAN TRACKING DEVICE FOR HOSPITALS, NURSING HOMES, AND PRIVATE USE

(76) Inventor: Ravinder Khaira, Carmichael, CA (US)

( * ) Notice: Subject to any disclaimer, the term of this patent is extended or adjusted under 35 U.S.C. 154(b) by 394 days.

(21) Appl. No.: 12/888,867

(22) Filed: Sep. 23, 2010

(51) Int. Cl.
*G08B 1/08* (2006.01)

(52) U.S. Cl. ......... 340/539.13; 340/539.12; 340/539.11; 340/572.1; 340/10.1; 340/572.8; 340/572.9

(58) Field of Classification Search ............. 340/539.13, 340/539.12, 539.11, 572.1, 10.1, 572.8, 572.9
See application file for complete search history.

(56) References Cited

U.S. PATENT DOCUMENTS

| | | | |
|---|---|---|---|
| 6,169,494 B1 | 1/2001 | Lopes | |
| 6,176,425 B1 * | 1/2001 | Harrison et al. | 235/385 |
| 6,278,370 B1 | 8/2001 | Underwood | |
| 6,396,403 B1 | 5/2002 | Haner | |
| 6,563,417 B1 * | 5/2003 | Shaw | 340/10.1 |
| 7,034,690 B2 | 4/2006 | Chaco | |
| D547,227 S | 7/2007 | Del Valle | |
| 7,545,274 B2 * | 6/2009 | Coop | 340/572.1 |
| 2004/0080420 A1 | 4/2004 | Roberts | |
| 2007/0241908 A1 * | 10/2007 | Coop | 340/572.8 |

* cited by examiner

*Primary Examiner* — Travis Hunnings

(57) ABSTRACT

A tracking device for tracking a patient and providing patient data. The device features a base ring for securing around a patient's wrist or ankle, the base ring is locked via a tamper-detecting optical lock with an alarm component. A microprocessor with a memory component is disposed in the base ring. A universal serial bus port for transferring data to and from the memory component is operatively connected to the microprocessor. An active radio frequency identification (RFID) circuit with a unique signature is disposed in the base ring, the active RFID has an antenna adapted to send signals from the RFID circuit and receive signals for the RFID circuit, the active RFID circuit is adapted to autonomously transmit signals within a range to an external communication system via the antenna, the signals representing location of the active RFID and information stored on the memory component.

20 Claims, 6 Drawing Sheets

HUMAN TRACKING DEVICE FOR HOSPITALS, NURSING HOMES, AND PRIVATE USE

FIELD OF THE INVENTION

The present invention is directed to tracking systems, more particularly to a novel tracking device for managing patients in a hospital, nursing homes, or for private use.

BACKGROUND OF THE INVENTION

Patient tracking in hospitals is extremely difficult. Most hospitals use paper systems (e.g., charts, dry erase boards) or computer systems to manage patients, but patient tracking cannot be done in real-time. The present invention features a novel tracking device for tracking patients in a hospital. The tracking device of the present invention can help improve patient management and even help improve infant recovery if a kidnapping occurs. The tracking device of the present invention features an optical lock and a para-aramid synthetic fiber (e.g., Kevlar®) housing with a reinforced casing, making the device difficult to remove or break.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY

The present invention features a tracking device. In some embodiments, the device comprises a base ring formed from a first half ring pivotally attached to a second half ring via a hinge, the base ring can pivot between at least an open position and a closed position, the base ring is adapted to be secured around an individual's wrist or ankle, the base ring is constructed from a material comprising a para-aramid synthetic fiber; a locking means for securing the base ring in the closed position, the locking means is adapted to detect tampering; an alarm component disposed in the base ring; a microprocessor comprising software and a memory component, the microprocessor is operatively connected to the alarm component, the microprocessor is adapted to receive a first alarm input signal from the locking means when the locking means detects tampering whereupon the microprocessor sends a first alarm output command to the alarm component to active the alarm component, the memory component is adapted to temporarily store information; a universal serial bus (USB) port operatively connected to the microprocessor with the memory components, the USB port allows for data transfer to and from the memory component; an active radio frequency identification (RFID) circuit disposed in the base ring, the active RFID has a unique signature, the active RFID circuit is operatively connected to each the microprocessor and to an antenna disposed in the base ring, the antenna is adapted to send signals from the RFID circuit and receive signals for the RFID circuit, the active RFID circuit is adapted to autonomously transmit signals within a range to an external communication system via the antenna, the signals representing location of the active RFID and information stored on the memory component; and a power source operatively connected to at least the active RFID circuit.

In some embodiments, the base ring further comprises a reinforced casing (constructed from a material comprising para-aramid synthetic fiber. In some embodiments, the base ring has rounded edges for comfort. In some embodiments, the locking means is an optical lock.

In some embodiments, the memory component comprises flash memory, read-only memory, random access memory, or a combination thereof. In some embodiments, the information stored on the memory component includes a name, an age, a date of birth, a medical history, a physician name, a medical record, or a combination thereof. In some embodiments, the memory component comprises a protection mechanism to prevent unwanted modification or unwanted erasing.

In some embodiments, the external communication device is a personal digital assistant (PDA) system or a hospital alert system. In some embodiments, the range is between about 0 to 50 feet, between about 0 to 100 feet, between about 0 to 200 feet, between about 0 to 500 feet, between about 0 to 750 feet, between about 0 to 1000 feet, between about 0 to 1500 feet, or between about 0 to 2000 feet. In some embodiments, the power source is a rechargeable battery.

The present invention also features a method of verifying a patient's identification. In some embodiments, the method comprises presenting a patient with the aforementioned tracking device and communicating with the RFID circuit via an external communication system. The external communication system is adapted to download the patient information relayed from the memory component to the RFID circuit.

DESCRIPTION OF PREFERRED EMBODIMENTS

Figure 1:
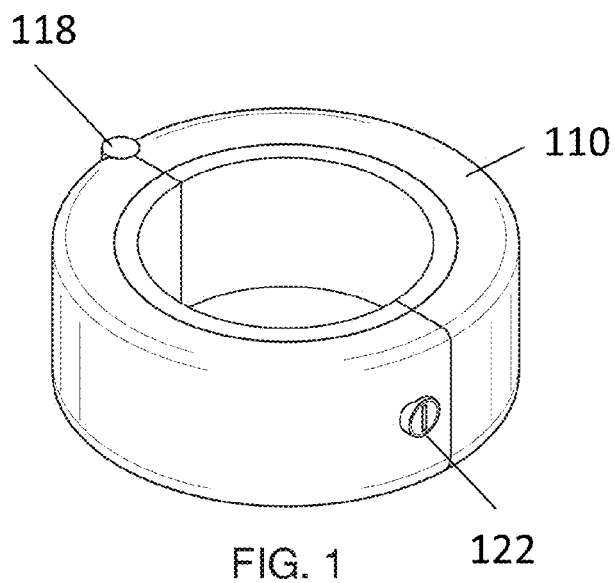
FIG. 1 is a front perspective view of the tracking device of the present invention.
Figure 2:
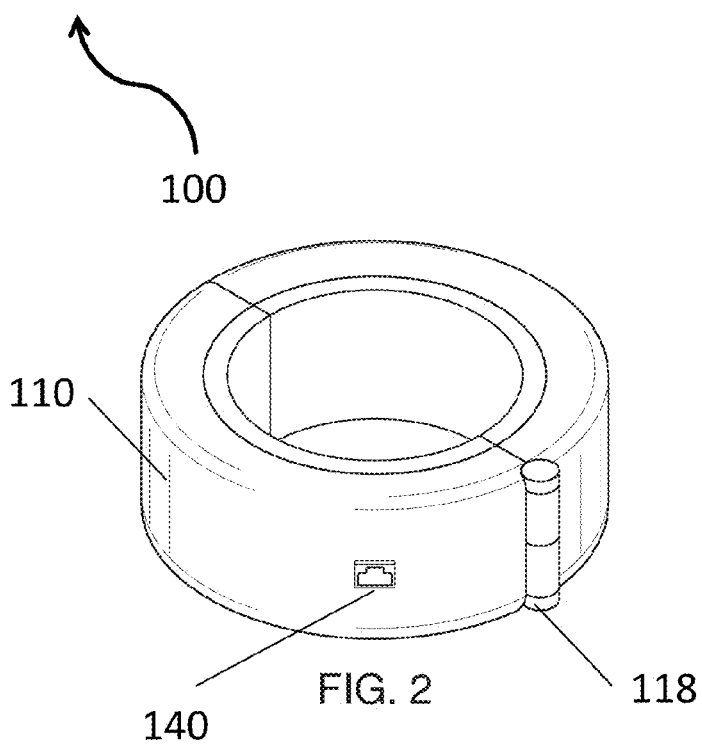
FIG. 2 is a back perspective view of the tracking device of the present invention.
Figure 3:
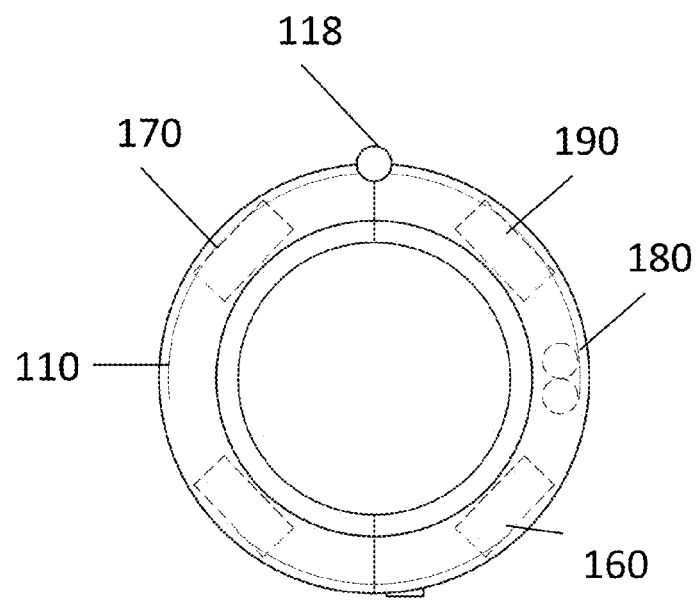
FIG. 3 is a first top view of the tracking device of FIG. 1, wherein the device is in the closed position.
Figure 4:
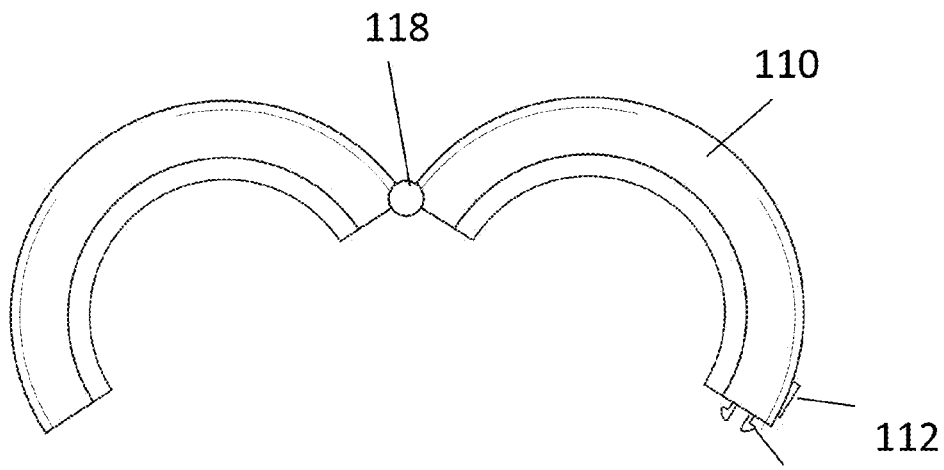
FIG. 4 is a second top view of the tracking device of FIG. 1, wherein the device is in the open position.
Figure 5:
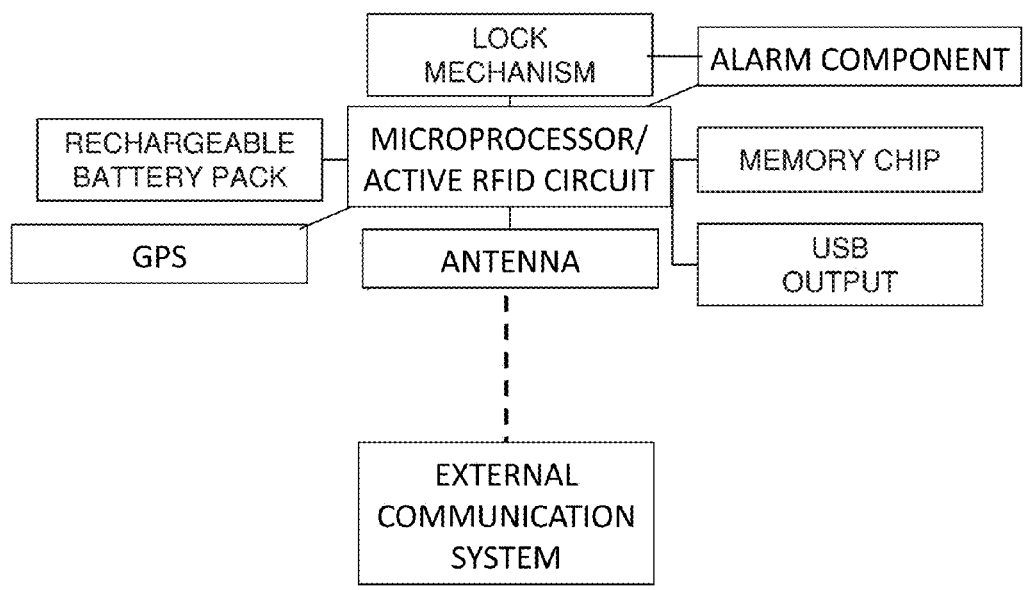
FIG. 5 is a schematic representation of the electrical components of the tracking device of the present invention.

Referring now to FIGS. 1-8, the present invention features a novel tracking device 100 for tracking patients (e.g., in a hospital) or other individuals. For example, in some embodiments, the device 100 of the present invention is used as a triage tool, a tracking tool for pediatric patients, a tracking tool for Alzheimer patents, or a means of providing and accessing medical records for managing patient information and patient care. The device 100 can even be used outside a medical facility, such as in a home. The device 100 may be particularly useful for physicians because the physicians can not only locate a patient (e.g., if the patent has moved to a different room suddenly) but access the patient's medical information as well.

The tracking device 100 comprises a base ring 110 divided into a first half ring and a second half ring. The base ring 110 is for securing around an individual's wrist or ankle (e.g., an adult, an infant, etc.). The first half ring and second half ring are pivotally connected via a hinge 118. The device 100 (e.g., the first half ring and second half ring) can pivot between an open position (see FIG. 4) and a closed position (see FIG. 1, FIG. 2, FIG. 3). Generally, the base ring 100 is small and compact.

The base ring 110 of the device 100 may be constructed in a variety of materials. For example, in some embodiments, the base ring 110 is constructed from a material making it hard to break, for example a para-aramid synthetic fiber (e.g., Kevlar®). The base ring 110 may comprise a reinforced casing (e.g., an outer shell), which may be constructed from a para-aramid synthetic fiber. For example, the base ring 110 may be constructed from a metal skeleton (e.g., aluminum, lightweight aluminum) and be coated with an outer shell of para-aramid synthetic fiber. The housing may be generally lightweight. In some embodiments, the edges of the base ring 110 are rounded for comfort. Edges of the device 100 may be reinforced for security.

Without wishing to limit the present invention to any theory or mechanism, it is believed that the base ring 110 is advantageous because it is extremely durable (e.g., constructed from para-aramid synthetic fibers), form fitting, and can be used in a variety of ways, for example as an ankle bracelet or a wrist bracelet.

The device 100 can be secured in the closed position via a locking means 120. The locking means 120 is difficult to break. In some embodiments, the locking means 120 includes an optical lock. In some embodiments, the locking means 120 can be unlocked via a key mechanism, for example a keyhole 122 is disposed in the base ring 110. The present invention is not limited to a key mechanism, for example the locking means 120 may include a combination lock, a magnetic lock, a constriction mechanism, the like, or a combination thereof.

The locking means 120 (e.g., optical lock) is operatively connected to an alarm component 190. The locking means 120 (e.g., optical lock) is configured to detect tampering (e.g., breakage). When the locking means 120 (e.g., optical lock) detects tampering the locking means 120 (e.g., optical lock) sends a first alarm input signal to the alarm component to activate the alarm component 190. This alerts others that the user is attempting to break free of the device 100. In some embodiments, the locking means 120 (e.g. optical lock) is operatively connected to a microprocessor, which is operatively connected to the alarm component 190. The microprocessor is adapted to receive a first alarm input signal from the locking means 120 (e.g., optical lock) when the locking means 120 (e.g., optical lock) detects tampering, whereupon the microprocessor sends a first alarm output command to the alarm component 190 to active the alarm component.

An active radio frequency identification (RFID) circuit 160, a power source 180 (e.g., a rechargeable battery), and a microprocessor are each disposed in the base ring 110. The microprocessor comprises software and memory components (e.g., flash memory, read-only memory, random access memory, etc.). The memory components are adapted to store information, for example patient information (e.g., name, date of birth, medical history, etc.). The memory can be erased and replaced with new information as necessary.

The active RFID circuit 160 is operatively connected to the microprocessor and to an antenna disposed in the base ring 110. The antenna is adapted to send signals from the RFID circuit 160 and receive signals for the RFID circuit 160. The active RFID circuit 160 is adapted to autonomously transmit signals.

RFID circuits are well known to one of ordinary skill in the art. For example, RFID circuits are generally used to track and identify cargo. The active RFID circuit 160 is configured to locate an individual and provide information about the individual via a unique identification (ID). An external communication device can communicate with the active RFIC circuit 160 wirelessly. In some embodiments, the device 100 of the present invention is configured to communicate with a personal digital assistant (PDA) system.

The device 100 of the present invention further comprises a universal serial bus (USB) port 140 operatively connected to the microprocessor (and memory components thereof). USB ports are well known to one of ordinary skill in the art. For example, the USB port 140 allows for data transfer to and from the memory component of the microprocessor, for example patient information, medical records, etc. The memory of the microprocessor may include but is not limited to flash memory, random access memory, and read-only memory.

In some embodiments, the memory of the microprocessor is protected to prevent modification or erasing by unauthorized parties. Examples of protection mechanisms include encryption, password protection, and the like.

The RFID circuit 160 of the present invention is adapted to send signals via the antenna to an external communication system within a range (e.g., 0 to 50 feet, 0 to 100 feet, 0 to 200 feet, 0 to 500 feet, 0 to 750 feet, 0 to 1000 feet, 0 to 1500 feet, 0 to 2000 feet, etc.). In some embodiments, the external communication system is a hospital alert system (e.g., at a nurses' station, etc.) In some embodiments, the hospital alert system is adapted to detect failure to receive the signal from the RFID circuit 160, thereby activating the hospital alert system alarm to alert individuals the patient has left the intended range. Thus, when the RFID circuit 160 is removed from the range, the hospital alert system alarm is activated.

The memory component of the microprocessor may store information including but not limited to an individual's name, age, date of birth, medical information, chart information, medical records, family information, physician's name, the like, or a combination thereof.

In some embodiments, the device 100 is constructed to resemble aesthetically appealing jewelry.

In some embodiments, the device 100 further comprises a global positioning system (GPS) 170.

Without wishing to limit the present invention to any theory or mechanism, it is believed that the device 100 of the present invention is advantageous because the device allows patent data to be stored on the device and also allows another individual to find the patient (e.g., if the patient is moved to a different room, for example).

EXAMPLE 1

Figure 6:
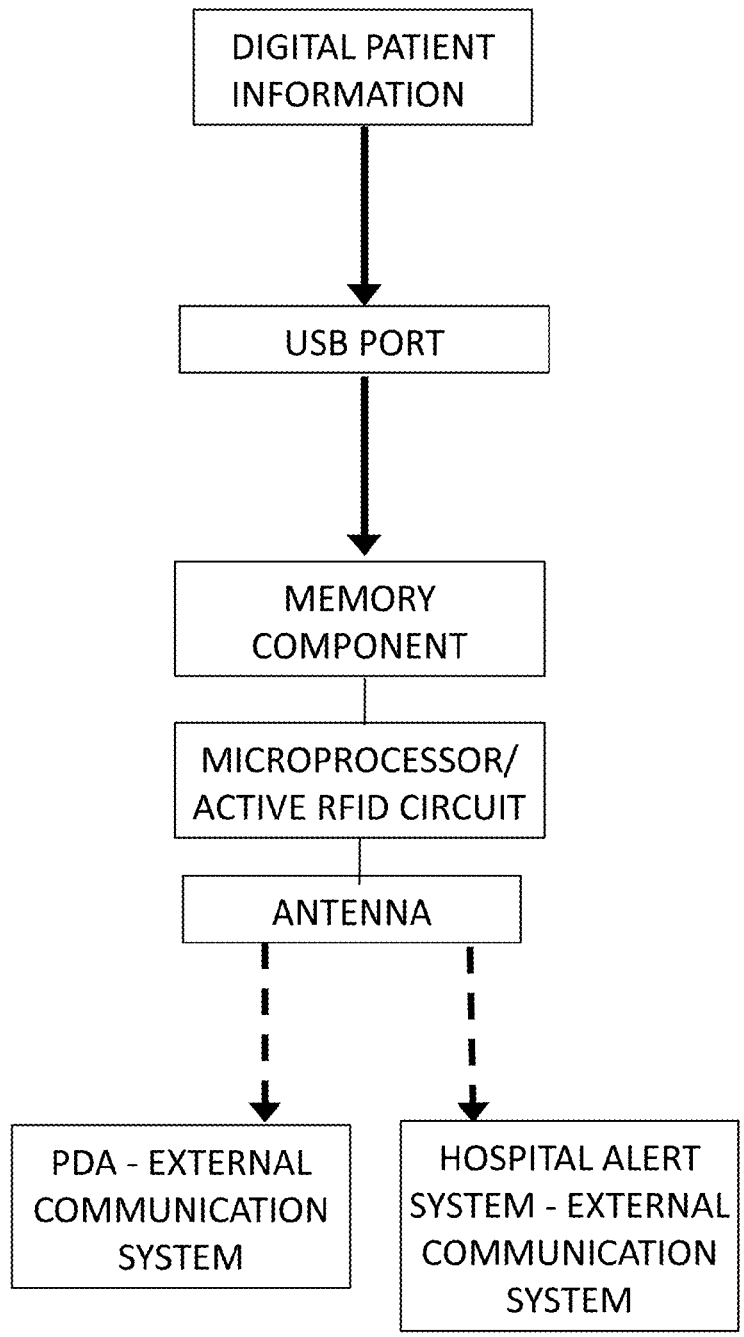
FIG. 6 is a schematic representation of the use of the device of the present invention.
Figure 7:
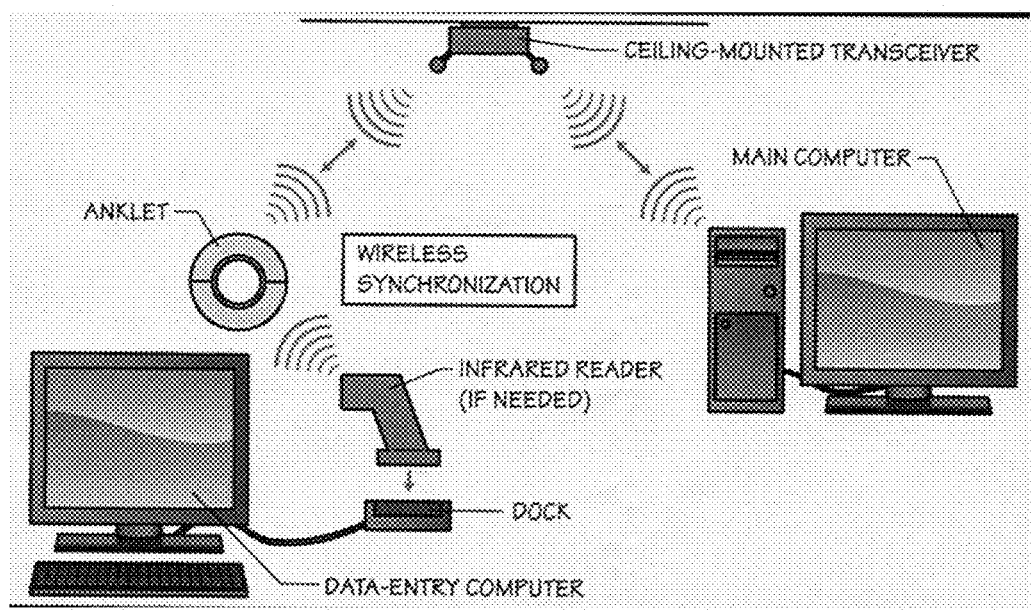
FIG. 7 is a schematic representation of the tracking device of the present invention. The device is in communication with external communication systems (e.g., main computer, data entry computer, PDA, alarm system, infrared reader, etc.) via a transceiver. For example, a signal from the device is sent to the transceiver, which distributes the signal to the external communication systems, and vice versa.
Figure 8:
FIG. 8 is an in-use view of the tracking device of the present invention as used on an individual's wrist or on a baby's ankle.

The following example describes a use of the device 100 of the present invention (e.g., as shown in FIG. 6). The present invention is not limited to the described example.

A hospital staff member enters patient date into the memory component of the device 100 via the USB port. The device 100 has a unique RFID signature. The hospital staff member places the device 100 onto the patient's wrist and locks the optical lock. A physician subsequently searches for the patient using his PDA system, which detects the location of the device via the active RFID circuit. The physician then uses the PDA system to download the patient's information stored on the memory component of the device 100.

The disclosures of the following U.S. Patents are incorporated in their entirety by reference herein: U.S. Provisional Pat. Application Ser. No. 61/077,018; U.S. Pat. No. 6,396,403; U.S. Pat. No. 6,278,370; U.S. Pat. No. 6,169,494; U.S. Pat. Application No. 2004/0080420; U.S. Pat. No. 7,034,690; U.S. Design Pat. No. D547,227.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A tracking device comprising:
   (a) a base ring formed from a first half ring pivotally attached to a second half ring via a hinge, the base ring can pivot between at least an open position and a closed position, the base ring is adapted to be secured around an individual's wrist or ankle, the base ring is constructed from a material comprising a para-aramid synthetic fiber;
   (b) a locking means for securing the base ring in the closed position, the locking means is adapted to detect tampering;
   (c) an alarm component disposed in the base ring;
   (d) a microprocessor comprising software and a memory component, the microprocessor is operatively connected to the alarm component, the microprocessor is adapted to receive a first alarm input signal from the locking means when the locking means detects tampering whereupon the microprocessor sends a first alarm output command to the alarm component to active the alarm component, the memory component is adapted to temporarily store information;
   (e) a universal serial bus (USB) port operatively connected to the microprocessor with the memory components, the USB port allows for data transfer to and from the memory component;
   (f) an active radio frequency identification (RFID) circuit disposed in the base ring, the active RFID has a unique signature, the active RFID circuit is operatively connected to each the microprocessor and to an antenna disposed in the base ring, the antenna is adapted to send signals from the RFID circuit and receive signals for the RFID circuit, the active RFID circuit is adapted to autonomously transmit signals within a range to an external communication system via the antenna, the signals representing location of the active RFID and information stored on the memory component; and
   (g) a power source operatively connected to at least the active RFID circuit.

2. The tracking device of claim 1, wherein the base ring further comprises a reinforced casing (constructed from a material comprising para-aramid synthetic fiber.

3. The tracking device of claim 1, wherein the base ring has rounded edges for comfort.

4. The tracking device of claim 1, wherein the locking means is an optical lock.

5. The tracking device of claim 1, wherein the memory component comprises flash memory, read-only memory, random access memory, or a combination thereof.

6. The tracking device of claim 1, wherein the information stored on the memory component includes a name, an age, a date of birth, a medical history, a physician name, a medical record, or a combination thereof.

7. The tracking device of claim 1, wherein the memory component comprises a protection mechanism to prevent unwanted modification or unwanted erasing.

8. The device of claim 1, wherein the external communication device is a personal digital assistant (PDA) system.

9. The device of claim 1, wherein the external communication system is a hospital alert system.

10. The device of claim 1, wherein the range is between about 0 to 50 feet, between about 0 to 100 feet, between about 0 to 200 feet, between about 0 to 500 feet, between about 0 to 750 feet, between about 0 to 1000 feet, between about 0 to 1500 feet, or between about 0 to 2000 feet.

11. The tracking device of claim 1, wherein the power source is a rechargeable battery.

12. A method of verifying a patient's identification, said method comprising:
   (a) presenting a patient with a tracking device, said tracking device comprising (i) a base ring formed from a first half ring pivotally attached to a second half ring via a hinge, the base ring can pivot between at least an open position and a closed position, the base ring is secured around the patient's wrist or ankle, the base ring is constructed from a material comprising a para-aramid synthetic fiber; (ii) a locking means for securing the base ring in the closed position, the locking means is adapted to detect tampering; (iii) an alarm component disposed in the base ring; (iv) a microprocessor comprising software and a memory component, the microprocessor is operatively connected to the alarm component, the microprocessor is adapted to receive a first alarm input signal from the locking means when the locking means detects tampering whereupon the microprocessor sends a first alarm output command to the alarm component to active the alarm component, the memory component is adapted to temporarily store patient information; (v) a universal serial bus (USB) port operatively connected to the microprocessor with the memory components, the USB port allows for data transfer to and from the memory component; (vi) an active radio frequency identification (RFID) circuit disposed in the base ring, the active RFID has a unique signature, the active RFID circuit is operatively connected to each the microprocessor and to an antenna disposed in the base ring, the antenna is adapted to send signals from the RFID circuit and receive signals for the RFID circuit, the active RFID circuit is adapted to autonomously transmit signals within a range to an external communication system via the antenna, the signals representing location of the active RFID and information stored on the memory component; and (vii) a power source operatively connected to at least the active RFID circuit; and
   (b) communicating with the RFID circuit via an external communication system, the external communication system is adapted to download the patient information relayed from the memory component to the RFID circuit.

13. The method claim 12, wherein the locking means is an optical lock.

14. The method claim 12, wherein the memory component comprises flash memory, read-only memory, random access memory, or a combination thereof.

15. The method claim 12, wherein the information stored on the memory component includes a name, an age, a date of birth, a medical history, a physician name, a medical record, or a combination thereof.

16. The method claim 12, wherein the memory component comprises a protection mechanism to prevent unwanted modification or unwanted erasing.

17. The method claim 12, wherein the external communication device is a personal digital assistant (PDA) system.

18. The method claim 12, wherein the external communication system is a hospital alert system.

19. The method claim 12, wherein the range is between about 0 to 50 feet, between about 0 to 100 feet, between about 0 to 200 feet, between about 0 to 500 feet, between about 0 to 750 feet, between about 0 to 1000 feet, between about 0 to 1500 feet, or between about 0 to 2000 feet.

20. The method claim 12, wherein the power source is a rechargeable battery.

* * * * *